(12) United States Patent
Malin et al.

(10) Patent No.: US 6,472,144 B2
(45) Date of Patent: Oct. 29, 2002

(54) HIGH THROUGHPUT SCREENING METHOD AND APPARATUS

(75) Inventors: Patricia J. Malin, Palo Alto; Kenneth R. Wada, San Jose; Peter J. Dehlinger, Palo Alto, all of CA (US)

(73) Assignee: Cellstat Technologies, Inc., Belmont, CA (US)

( * ) Notice: Subject to any disclaimer, the term of this patent is extended or adjusted under 35 U.S.C. 154(b) by 0 days.

(21) Appl. No.: 09/813,922

(22) Filed: Mar. 20, 2001

(65) Prior Publication Data

US 2002/0025575 A1 Feb. 28, 2002

Related U.S. Application Data

(62) Division of application No. 09/202,658, filed as application No. PCT/US97/11211 on Jun. 26, 1997, now Pat. No. 6,235,520.
(60) Provisional application No. 60/021,074, filed on Jun. 27, 1996.

(51) Int. Cl.$^7$ ............................. C12Q 1/00; C12M 1/34; G01N 27/00
(52) U.S. Cl. ..................... 435/4; 435/287.1; 435/288.4; 422/82.01; 422/82.02; 204/400; 204/403
(58) Field of Search ...................... 435/4, 287.1, 288.4; 422/82.01, 82.02; 204/400, 403

(56) References Cited

U.S. PATENT DOCUMENTS 5,643,742 A * 1/1997 Malin et al. .................. 435/29
6,235,520 B1 * 5/2001 Malin et al. ............. 435/287.1

FOREIGN PATENT DOCUMENTS

WO          97/49987      * 12/1997

* cited by examiner

*Primary Examiner*—Louise N. Leary
(74) *Attorney, Agent, or Firm*—David J. Brezner; David C. Foster; Dorsey & Whitney LLP

(57) ABSTRACT

High-throughput screening method and apparatus are described. The method includes placing cells on a substrate defining a plurality of discrete microwells, at a well density of greater than about 100/cm$^2$, with the number of cells in each well being less than about 1000, and where the cells in each well have been exposed to a selected agent. The change in conductance in each well is determined by applying a low-voltage, AC signal across a pair of electrodes paced in that well, and synchronously measuring the conductance across the electrodes, to monitor the level of growth or metabolic activity of cells contained in each well. Also disclosed is an apparatus for carrying out the screening method.

5 Claims, 3 Drawing Sheets

HIGH THROUGHPUT SCREENING METHOD AND APPARATUS

This is a divisional of U.S. application Ser. No. 09/202,658, filed May 14, 1999, now U.S. Pat. No. 6,235,520, which is a 371 of PCT/US97/1121, filed Jun. 26, 1997 and claims the benefit of U.S. application Ser. No. 60/021,074, filed Jun. 27, 1996, which applications are incorporated herein by reference and to which applications priority is claimed under 35 USC § 120 and 119.

FIELD OF THE INVENTION

The present invention relates to high throughput screening (HTS) methods, e.g., for detecting the effect of a given compound or treatment on cell metabolic activity, and apparatus for performing such screening.

BACKGROUND OF THE INVENTION

With the advent of combinatorial library methods for generating large libraries of compounds, there has been a growing interest in high-throughput screening (HTS) methods for screening such libraries.

The most widely used HTS screening method involves competitive or non-competitive binding of library compounds to a selected target protein, such as an antibody or receptor. Thus, for example, to select a library compound capable of blocking the binding of a selected agonist to a receptor protein, the screening method could assay for the ability of library compounds to displace radio-labeled agonist from the target protein.

Although such binding assays can be used to rapidly screen large numbers of compounds for a selected binding activity, the assay itself may have limited relevance to the actual biological activity of the compound in vivo, e.g., its ability to interact with and affect the metabolic behavior of a target cell.

It would therefore be useful to provide high throughput screening methods capable of testing the effects of large numbers of library compounds on target cells of interest.

SUMMARY OF THE INVENTION

The invention includes, in one aspect, high throughput screening apparatus, e.g., for screening the effect of test compound on cell metabolic activity, or for screening the effect of a genetic manipulations on cells. The apparatus includes a multiwell device defining a plurality of discrete microwells on a substrate surface, at a well density of greater than about 100/cm$^2$, where the well volumes are such as to accommodate at most about 10$^6$ cells/well, preferably between 1–100 wells/cell, and structure for measuring the conductance in each well. The measuring structure includes (i) a pair of electrodes adapted for insertion into a well on the substrate, and (ii) circuitry for applying a low-voltage, AC signal across the electrodes, when the electrodes are submerged in the medium, and for synchronously measuring the current across the electrodes, to monitor the level of growth or metabolic activity of cells contained in the chamber.

In various preferred embodiments, the signal circuitry is effective to generate a signal whose peak-to-peak voltage is between 5 and 10 mV, and includes feedback means for adjusting the signal voltage level to a selected peak-to-peak voltage between 5 and 10 mV.

In other embodiments, the circuitry is designed to sample the voltage of the applied signal at a selected phase angle of the signal, or alternatively, to sample the voltage of the applied signal at a frequency which is at least an order of magnitude greater than that of the signal.

In another general aspect, the invention includes a high-throughput screening method, e.g., for screening the effect of test compounds on cell metabolic activity, or the effect of a given genetic manipulation. The method includes placing cells in the wells of a multiwell device defining a plurality of discrete microwells on a substrate surface, at a well density of greater than about 100/cm$^2$, with the number of cells in each well being less than about 10$^6$, and preferably between 1–10$^3$. The conductance in each well is determined by applying a low-voltage, AC signal across a pair of electrodes placed in the well, and synchronously measuring the conductance across the electrodes.

These and other objects and features of the invention will become more fully apparent when the following detailed description of the invention is read in conjunction with the accompanying drawings.

DETAILED DESCRIPTION OF THE INVENTION

A. Screening Apparatus and Method

Figure 1:
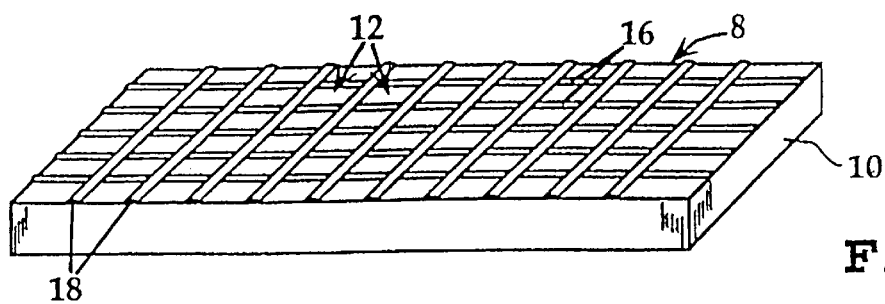
FIG. 1 is a perspective view of a multiwell device that forms part of the apparatus of the invention.

FIG. 1 shows a perspective view of a multiwell device 8 formed of a substrate 10 having a plurality of microwells, such as wells 12, on the upper substrate surface 14. In the embodiment shown, the microwells are formed by a grid of hydrophobic lines, such as lines 16 extending lengthwise, and lines 18 extending widthwise. The lines are preferably formed of a hydrophobic polymer material, such as polyethylene or polystyrene, and are laid down in a conventional manner, e.g., deposition of melted polymer from an applicator, or heat-mediated attachment of a polymer grid fabric directly to the substrate surface.

Spacing between adjacent parallel lines is preferably 20–200 μm, so that the wells formed by intersecting lines have area dimensions of between about 400 to 40,000 μm$^2$. The density of wells on the substrate is at least 100/cm$^2$ and more preferably 10$^3$/cm$^2$ to 10$^4$/cm or greater.

Figure 2A:
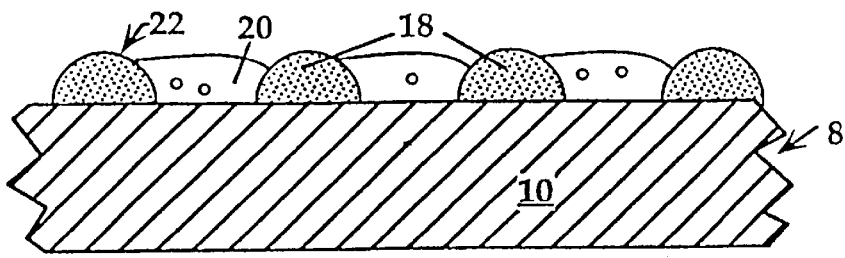
FIG. 2A is an enlarged, fragmentary cross-sectional view of the device in FIG. 1, with the wells in the device each containing a small number of cells suspended in a culture medium.
Figure 2B:
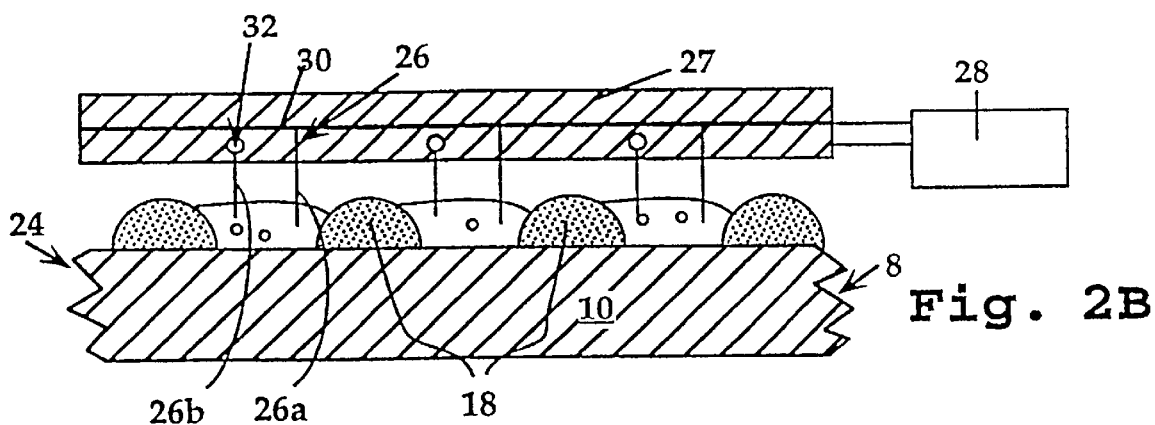
FIG. 2B is a view like that in FIG. 2A, but further showing an electrode cover on the device.

The height (surface relief) of the grid lines, seen best in FIGS. 2B and 2B, is typically between 20–200 μm. Microwell volumes, defined by the volume that can be held as a discrete droplet in a microwell, are typically in the range $10^{-4}$ to 2 nonoliters.

The microwells in the device may be filled with selected biological cells by applying a suspension of the cells, at a desired cell density, over the device's surface, and allowing excess suspension fluid to drain off, e.g., by blotting the edges of the device. This is illustrated in FIGS. 2A and 2B which show cell suspension droplets, such as droplet 20, in the microwells of the device, such as microwell 22. It will be appreciated that the droplet meniscus may extend above the height of the grid lines.

The cell density is adjusted so that the wells are filled, on average, with a selected number of cells which is preferably between 1–100, but may be as high as $10^3$ per well. As illustrated in FIGS. 2A and 2B, the density of the cells is such that the device has an average of about 2 cells/well. A greater number of cells/well, e.g., an average of 10–100/well provides improved statistical correlation among events observed in different cells, due to more uniform cell-number distribution in the microwells of the device. At the same time, a small number of cells, e.g., 10–100, allows a microwell (microvolume) format in which desired concentrations of test compounds can be achieved with very small amounts of compound, e.g., in the femptogram to nonogram range. The actual number of cells employed will depend on the particular type of cell and medium, and the confluency requirements of the cells.

With reference particularly to FIG. 2B, the apparatus of the invention, further includes means for measuring the conductance of the cell medium in each well. In the embodiment shown, this means includes a multi-electrode cover 27 having a plurality of electrodes pairs, such as electrode pair 26 made up of electrodes 26a, 26b formed as a grid on the lower side of the cover. Specifically, the grid of electrode pairs matches that of microwells in device 8, so that the placement of the cover on the device places an electrode pair in each microwell.

The measuring means also includes a signal unit 28 electrically connected to the cover as described below with reference to FIG. 3. The operation of the unit to provide a low-voltage AC signal to each electrode, and interrogate the electrode to determine the conductance in each microwell is described below with reference to FIGS. 6 and 7.

Figure 3:
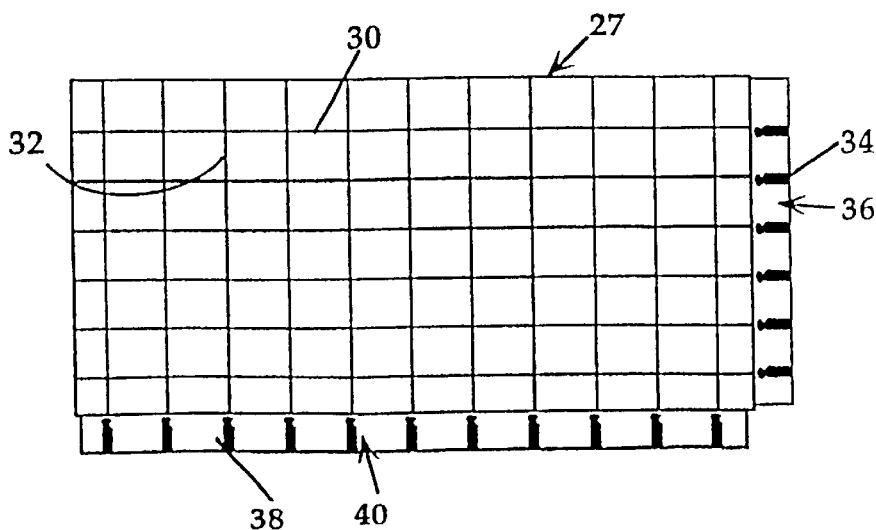
FIG. 3 illustrates the grid of conductive wires in the electrode plate shown in FIG. 2B.

FIG. 3 is a plan view of cover 27, showing the grid pattern of conductive wires, such as longitudinal wires 30, and lateral wires 32, connecting the electrode pairs in the cover. Each longitudinal wire is connected to an electrode connector, such as wires 32 connected to connectors 34, in a multi-connector array 36 along one side of the cover, as shown. Similarly, each lateral wire is connected to an electrode connector, such as wires 32 connected to connectors 38, in a multi-connector array 40 along another side of the cover. The two arrays are designed to plug into matching ports in the signal unit.

As seen in FIG. 2B, each longitudinal wire, such as wire 30, is electrically connected to one of the two electrodes in the longitudinal one-dimensional array of electrode pairs, such as the array including pair 26, adjacent the wire. Similarly, each lateral wire, such as wire 36, is electrically connected to one of the two electrodes in the lateral one-dimensional array of electrode pairs, such as the array including pair 26, adjacent that wire.

Thus, to interrogate a particular microwell in the device, the signal unit applies a low-voltage signal across the two connectors in cover 27 which are connected to the two electrodes in that well. For example, to interrogate microwell 26 in FIG. 2B, the signal unit applies a voltage signal across connectors 34, 38 connected to electrodes 26a, 26b, respectively, forming the electrode pair in that microwell. To this end, the signal unit includes the basic electronics for applying a low-voltage signal to the electrodes, and for synchronously measuring the current across the electrodes, as described below.

Unit 28 also includes conventional multiplexing or sampling circuitry for alternately and successively interrogating each microwell, by applying a short duration signal to successively to each well, and measuring the current across the "stimulated" electrodes in accordance with the signalling and current measuring procedures described below. According to one feature of the signal unit, the time required accurately interrogate each microwell can be quite short, on the order of only a few cycles on the applied signal, allowing large arrays to be continuously monitored in real time.

Figure 4A:
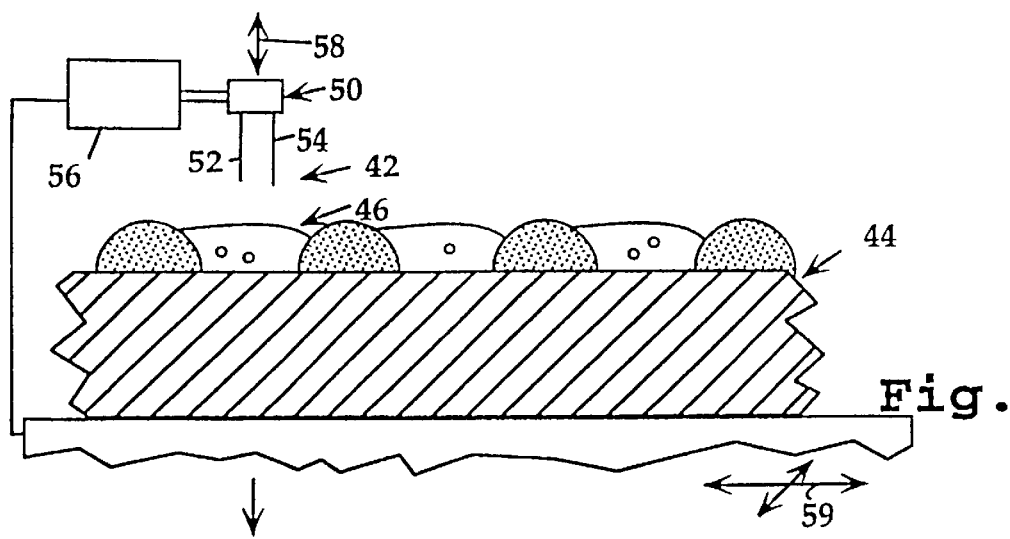
FIGS. 4A–4C illustrate another embodiment of the apparatus, here designed for well-by-well conductance measurements.
Figure 4B:
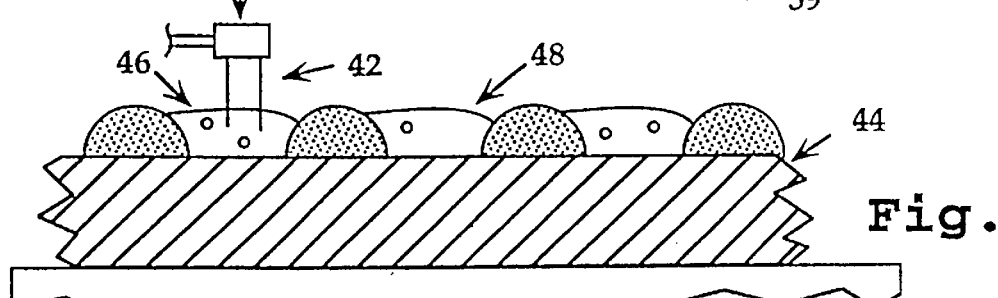
Figure 4C:
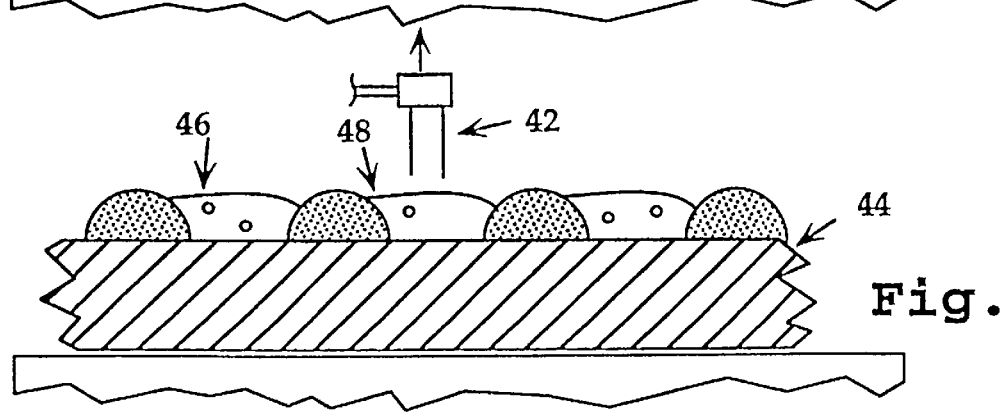

FIGS. 4A–4C illustrate a HTS apparatus 42 constructed according to another embodiment of the invention. The apparatus includes a multiwell device 44 similar to above described device 8, and having a planar array of microwells, such as wells 46, 48. In this embodiment, however, the measuring means for determining the conductance of each well is carried out by an electrode arm 50 having a pair of electrodes 52, 54 adapted to be received in a selected microwell of the device, and connected to a signal unit 56. The electrode arm is movable in the "z" plane between raised and lowered positions in which the electrodes are position above, and in a selected microwell, respectively, as illustrated in FIGS. 4A and 4B, respectively. This movement is produced by a vertical actuator, indicated by arrow 58, which is also under the control of unit 50.

Also forming part of the apparatus is a stage 60 on which the device is placed during operation. The stage is movable, in an "x-y" plane under the control of signal unit 56, to alternatively and successively bring each microwell in the device to an interrogation position directly below the electrode arm, as indicated for well 46 in FIGS. 4A and 4B. The signal unit also includes the basic electronics for applying a low-voltage signal to the electrodes, and for synchronously measuring the current across the electrodes, as described below.

In an exemplary operation, for use in screening combinatorial library compounds, and with reference particularly to the embodiment shown in FIGS. 1–3, the microwells in the device are filled with a cell suspension, as above, and the library compounds are added to each of wells, either before or after cell addition. For example, using microfabrication techniques of the type described in U.S. Pat. No. 5,143,854, a position-addressable planar array of polymer library molecules is formed on a planar substrate—in this case having or subsequently prepared to have a hydrophobic grid forming the microwells, which correspond to the individual library-polymer regions. After addition of the cells, the library compounds may be released for interaction with the cells, e.g., by inclusion in the cell suspension of an enzyme capable of cleaving the library molecules from the substrate surface.

Alternatively, the library compounds may be contained on a grid of pins or the like corresponding to the microwell grid, allowing the compounds to be simultaneously introduced into the wells, and released into the corresponding wells, e.g., by enzymatic cleavage of a linker.

Alternatively, the library compounds may be distributed well-by-well into the microwell device, either as single compounds or mixtures of library compounds.

Figure 5:
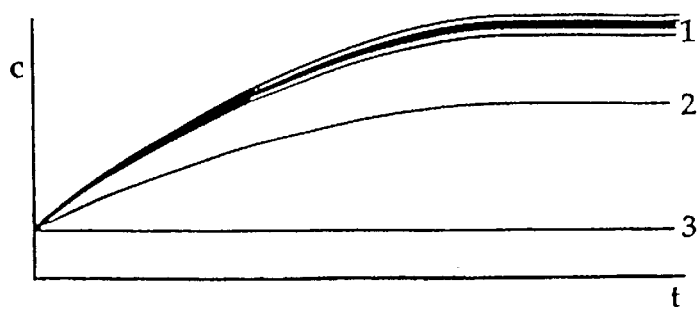
FIG. 5 shows idealized plots of conductance, as a function of time, in the presence and absence of a library compound that inhibits cell growth or metabolism.

After introducing the compound to be tested, the microwells are interrogated to determine the conductance of medium in each cell, by measuring the current across the electrodes. In the present example, it is assumed that (i) a large number of individual library compounds are added to the device, one per well, and (ii) one or more of the compounds is able to inhibit metabolic activity and/or replication of the cells. In the absence of any inhibition, cell metabolism and growth will occur normally, leading to an increase in measured conductance over time, as illustrated by plot number 1 in FIG. 5. Since only a few of the test compounds will be expected to have an inhibitory effect, most or nearly all of the plots will be represented by the "normal" plot.

Where an inhibitory compound is present, this will be evidenced by a lower rate of conductance change over time, as indicated by curves 2 and 3 in FIG. 5, where curve 2 represents moderate inhibition, and curve 3, nearly complete inhibition. The reduced conductance may be due to reduced metabolism and/or reduced replication. To confirm the latter possibility, the microwells of interest may be further examined for cell count, using standard cell counting methods.

In another general embodiment, the screening method is employed to monitor the success of a selected genetic manipulation, e.g., transformation of the cells with a selected vector, treatment with a transforming virus such as EBV, or cell fusion. In this embodiment, the genetically manipulated cells are distributed on the microwell device as above, and changes in cell conductance, related to cell replication are monitored. Those wells that show significant increase in cell conductance over time are then selected as cells which are successfully manipulated. Thus, for example, if the cells are transformed with a vector containing a selectable antibiotic marker gene, cells which grow in the presence of the antibiotic can be readily identified by the increased conductance in the corresponding microwell(s).

B. Signal Unit Construction and Operation

Figure 6:
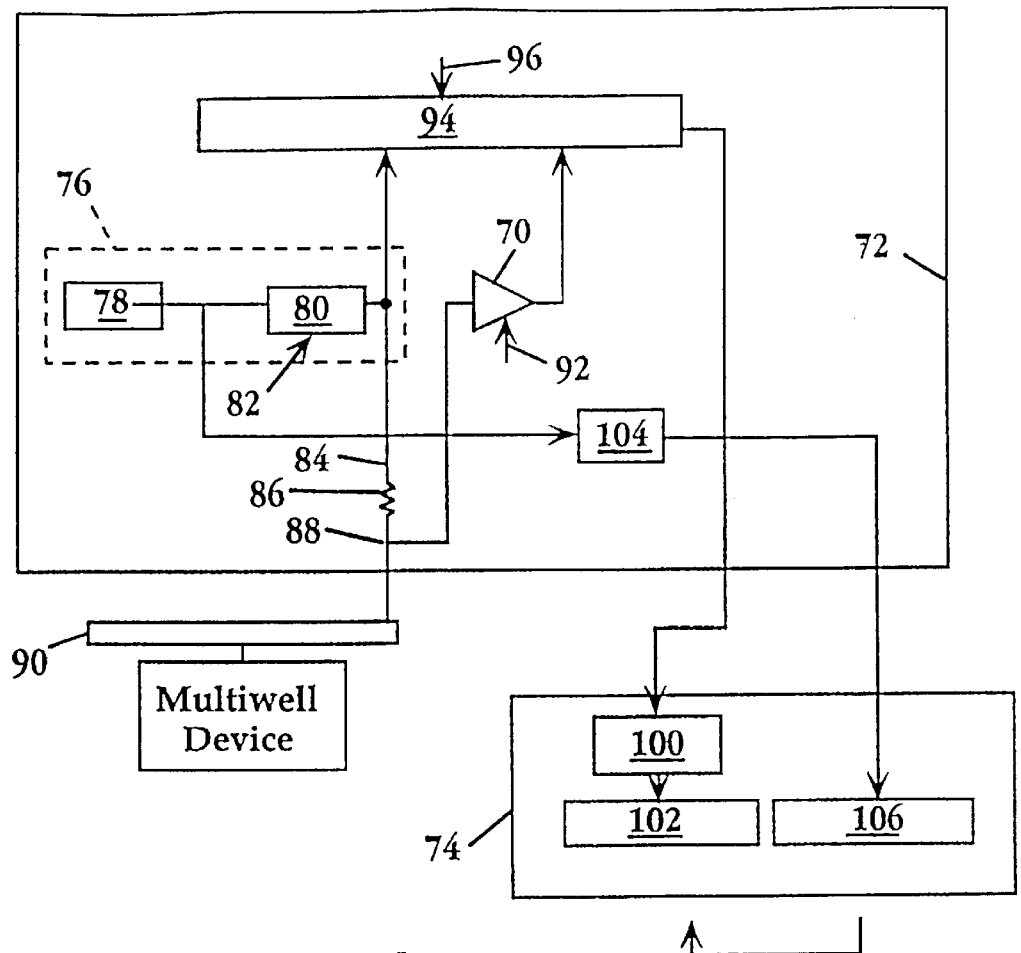
FIG. 6 is a block diagram depicting selected portions of the data acquisition board and of the measurement input/output board in accordance with the present invention.

FIG. 6 is a block diagram in accordance with one preferred embodiment of the present invention depicting a portion of the electronic circuit for applying the potential across a pair of pins or electrodes 26a, 26b, and for monitoring the current across the pins.

A computer program executed by a computer system included in the cell culture monitoring and recording system causes a programmable gain amplifier 70 included in a data acquisition board 72 to transmit a voltage representative of that applied across a pair of pins 26a, 26b inserted into a well for digitization by a measurement input/output board 74. The measurement input/output board 74 of the present embodiment is preferably a MetraByte DAS-8 Data Acquisition and Control Board marketed by Keithley Metrabyte Corporation of Taunton, Mass.

To supply the alternating current voltage that is applied across a selected pair of pins 26a, 26b, the data acquisition board 72 includes a programmable voltage source 76. The programmable voltage source 76 includes an alternating current generator 78 that produces a 370 Hz ±20%, 10 volt peak-to-peak sine wave signal. The output signal produced by the alternating current generator 78 is transmitted to a programmable attenuator 80 also included in the programmable voltage source 76. Digital excitation level control signals supplied from the computer system to the programmable attenuator 80 via excitation level control signal lines 82 permit adjustment of the peak-to-peak voltage supplied to a first terminal 84 of a resistor, such as a 20.04 K ohm resistor 86.

A second terminal 88 of the resistor 86 connects to a bank of switches 90. One of the switches 90 is selected by the computer system for applying the alternating current voltage supplied by the programmable voltage source 76 to a pair of pins 26a, 26b that extend into the well being monitored.

The AC voltage applied across a pair of pins 26a, 26b is also supplied to the input of the programmable gain amplifier 70. The gain of the amplifier 70 may be adjusted by control signals supplied from the computer system via gain control signal lines 92. The output signals from the programmable attenuator 80, and from the programmable gain amplifier 70 are both supplied to multiplexer 94. Control signals supplied from the computer system to multiplexer 94 via multiplexer control signal lines 96 select one of these three signals for application to an input of a sample-and-hold amplifier 100 included in the measurement input/output board 74.

The output signal from the sample-and-hold amplifier 100 is supplied to the input of an analog-to-digital converter 102 also included in the measurement input/output board 74. In addition to being supplied to the programmable attenuator 80, the 10 volt peak-to-peak output signal from the alternating current generator 78 is also supplied to the input of a comparator 104. The output signal from the comparator 104 changes state each time the alternating current voltage produced by the alternating current generator 78 passes through zero volts.

Thus, while the alternating current voltage produced by the generator 78 has a potential greater than zero volts, the output signal from the comparator 104 is in one state, and while that voltage has a potential less than zero volts, the output signal from the comparator 104 is in its other state. The output signal from the comparator 104 is supplied to a programmable timer 106 included in the measurement input/output board 74.

As described herein, the voltage present at the second terminal 88 of resistor 86 is applied across the two pins of a selected well 12 via a switch 90. This "pin voltage", which is proportional to the conductivity of the medium and the current flow between the two pins, is measured by the programmable gain amplifier 70. To efficiently obtain a reliable measurement of this voltage (and of the underlying current), the pin voltage is preferably sampled synchronously with the applied voltage. This can be done in several ways, two of which are described below.

1. Sampling at a selected phase angle.

Figure 7:
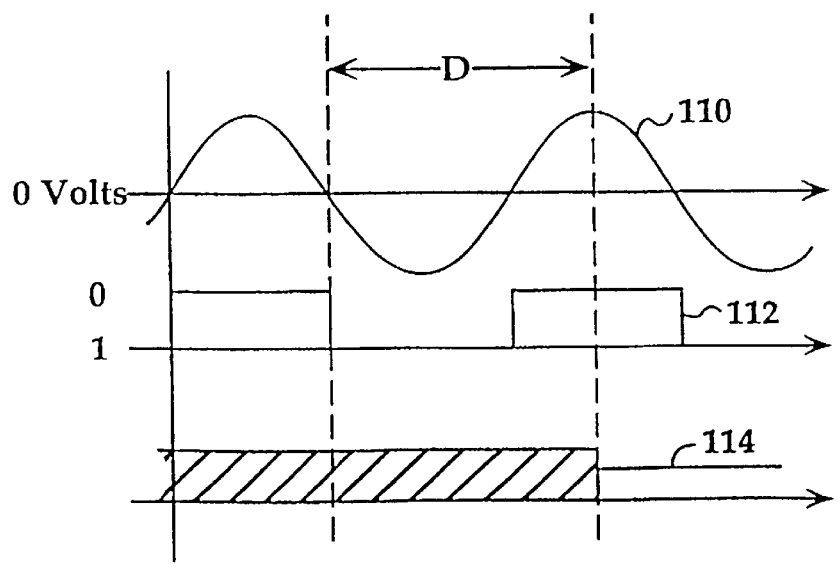
FIG. 7 depicts waveforms for the alternating current voltage supplied for application across a pair of pins, an output signal produced by a comparator in response to the alternating current voltage, and a hypothetical output signal from a sample-and-hold amplifier.

FIG. 7 depicts a sinusoidal alternating current waveform 110 for the voltage present at the output of the alternating current generator 78 together with the a digital waveform 112 of the output signal produced by the comparator 104. During initialization of the cell culture monitoring and recording system and at any subsequent time that it is requested by an operator of the cell culture monitoring and recording system, the computer program executed by the computer system executes a procedure for establishing a delay period ("D") of a selected duration that is shorter than one cycle of the sine waveform 110. For example, in FIG. 7, the delay period begins when the sine waveform 110 is changing from a positive potential to a negative potential has a potential of zero volts, and ends when the sine waveform 110 has its immediately subsequent maximum positive value.

In measuring the delay period D, the computer program uses the output signal from the comparator 104 in the data acquisition board 72 together with the programmable timer 106 included in the measurement input/output board 74 to determine the duration of one period of the sine waveform 110. The computer program then establishes the delay period D at three-fourths of one period of the sine waveform 110. Having determined a proper delay period D, the computer program then loads that delay period into the programmable timer 106 so that all subsequent measurements of the electrical potential across a pair of pins 26a, 26b will occur when the voltage supplied to the first terminal 84 of the resistor 86 reaches its maximum value, i.e., at the same selected phase angle of each cycle.

In measuring the voltage applied across a pair of pins 26a, 26b, the programmable timer 106 begins measuring each delay period at the instant at which the sine waveform 110 is changing from a positive potential to a negative potential has a potential of zero volts, i.e. immediately after the digital value of the output signal from the comparator 104 supplied to the programmable timer 106 changes from 0 to 1. When the delay period D expires, the programmable timer 106 causes the sample-and-hold amplifier 100 to sample and hold the voltage of the signal supplied from the output of the programmable gain amplifier 70 via the multiplexer 94 as illustrated in the waveform 114 depicted in FIG. 7.

The programmable timer 106 also causes the analog-to-digital converter 102 to convert the voltage of the analog signal received from the sample-and-hold amplifier 100 into a digital form. Subsequently, this digital number is transferred from the measurement input/output board 74 to the computer system for storage as raw data suitable for subsequent analysis and graphic display.

2. Sampling at a frequency which is at least an order of magnitude greater than the applied voltage.

Another way of synchronously sampling the pin voltage, which is proportional to the current across the electrodes, is to sample and digitize the signal at a frequency which is at least an order of magnitude greater than the applied voltage (termed "burst sampling"). In this mode of operation, the pin voltage is sampled an digitized a selected number of times (e.g., 10–1000) during a single cycle of the applied voltage. This can be accomplished, for example, by triggering the beginning and of storage of a string of digitized current values with the rising or falling transition of the digital waveform 112 of the output signal produced by the comparator 104. Such a digitized waveform can be analyzed with respect to the applied voltage using the computer system to calculate, for example, any phase lead or lag of the underlying current with respect to the applied voltage, as well as the peak-to-peak and/or RMS current values. These current values can in turn be used in the calculation of the conductance of the medium as described herein. An advantage of this approach is that an accurate estimate of the conductance can be obtained in a single cycle of the applied voltage, enabling rapid multiplex sampling of a plurality of samples.

Adjusting Voltage Applied Across a Pair of Pins.

In addition to performing the above, the program executed by the computer system also determines the alternating current voltage to be applied from the second terminal 88 of the resistor 86 across the pair of pins 26a, 26b during such monitoring. To determine this alternating current voltage, the computer program first adjusts the programmable attenuator 80 so a potential of approximately 10 millivolts is present at its output and at the first terminal 84 of the resistor 86. Because the 20.04 K ohm resistance of the resistor 86 separates its first terminal 84 from its second terminal 88, and because any cell growth media held in the well 12 provides some electrical conductivity between the pair of pins 26a, 26b inserted therein, initially the voltage at the second terminal 88 and across a pair of pin 26a, 26b must be less than the value of 10 millivolts intended to be used in measuring the conductivity between a pair of pins 26a, 26b. The computer program then causes the multiplexer 94 to select the output signal from the programmable gain amplifier 70 for application to the input of the sample-and-hold amplifier 100, sets the gain of the programmable amplifier 70 so a peak voltage of 120 millivolts at the second terminal 88 of the resistor 86 will result in the analog-to-digital converter 102 producing a digital number that is approximately 83.3% of the full range of the analog-to-digital converter 102, and causes the bank of switches 90 to select a pair of pins 26a, 26b for application of the alternating. current voltage.

The cell culture monitoring and recording system then measures the peak alternating current voltage present at the second terminal 88 of the resistor 86 that is applied across the pair of pins 26a, 26b. If the voltage at the second terminal 88 and across the pair of pins 26a, 26b is less than 5 millivolts, the computer program doubles the alternating current voltage produced by the programmable attenuator 80 repeatedly until the voltage measured at the second terminal 88 exceeds 5 millivolts. Having thus applied and measured an alternating current voltage across the pair of pins 26a, 26b that exceeds 5 millivolts and knowing the setting for the programmable attenuator 80 which produces that voltage, the computer program then computes a new setting for the programmable attenuator 80 that will apply approximately a 10 millivolt alternating current voltage to the second terminal 88 and across the pair of pins 26a, 26b, and then transmits control signals setting the attenuator 80 to the computed value.

Having established the value for the alternating currant voltage applied by the programmable attenuator 80 to the first terminal 84 of the resistor 86, the system is now prepared to monitor and record the electrical conductivity of the well 12. In measuring the conductivity of the well 12, the computer program first repetitively measures the voltage applied across the pair of pins 26a, 26b and at the second terminal 88 of the resistor 86. For example, applying the method of measuring at a selected phase angle, the computer system collects 16 successive values for this voltage, and the computer program then computes an average of the 16 values using a box-car filter to obtain a single, average value for the voltage across the pair of pins 26a, 26b. Alternatively, applying the burst sampling approach, a single, average value can be obtained from the RMS value of the digitized signal. Using the single value of the pin voltage, the value of the voltage supplied by the programmable attenuator 80 to the first terminal 84 of the resistor 86, and the resistance of the resistor 86; the computer program then computes the conductivity of the cell growth media and cells, if any, between the pair of pins 26a, 26b.

Having determined the conductivity between the pair of pins 26a, 26b for this well 12, the computer program first stores the conductivity value for subsequent analysis and then proceeds to measure the conductivity between another pair of pins 26a, 26b extending into another well 12 in the microwell device 8. In determining the conductivity of each well, the cell culture monitoring and recording system uses the procedures set forth above of first adjusting the alternating current voltage applied across the pair of pins 26a, 26b, and then measuring and averaging the voltage applied across the pair of pins 26a, 26b extending into the well 12. This adjusting of the applied voltage and determining of cell conductivity is repeated over and over until a conductivity has been determined and stored for all wells 12 in the microwell device 8.

At least one of the wells 12 in the microwell device 8 is preferably a reference well that holds only cell culture media without cells. Furthermore, this reference well must be specifically so identified to the analysis computer program because that program uses the conductivity value for the reference well in analyzing the conductivity for all the other wells.

Analysis of the conductivity of a well that held both cell growth media and cells included dividing the conductivity measured for the reference well by the conductivity measured for the well that held both the cell growth media and cells. Rather than using the electrical conductivity of the reference well as the numerator of a fraction analyzing the conductivity of a well that holds both cell growth media and cells, it has been found more advantageous in analyzing the conductivity of wells holding both cell growth media and cells to subtract the conductivity determined for the reference well from the conductivity determined for the well holding both cell growth media and cells. Subtracting the conductivity measured for the reference well, i.e. a well that holds only cell growth media without cells, from the conductivity measured for wells that holds both growth media and cells removes the electrical conductivity of the cell growth media from the data for such wells. Removing the cell growth media conductivity from the data for the well results in data values for the wells holding both cell growth media and cells that more closely represents the electrical conductivity of only the cells themselves, and the cells' metabolic products.

While the preferred embodiments of the present invention as described above employ a sinusoidal alternating current in monitoring cell cultures, it may be possible to employ any periodic voltage waveform that is symmetric about zero volts in determining conductivity between a pair of pins 26a, 26b. Thus, for example, a system for monitoring and recording cell cultures in accordance with the present invention could employ an alternating current voltage having a triangular waveform.

Since a triangular waveform alternating current voltage may be easily generated using a digital logic circuit, in a system employing such a waveform it would be unnecessary to directly measure, as described above, the delay period D. Rather the digital circuits used in generating the triangular waveform alternating current voltage could themselves directly produce signals for controlling the operation of the sample-and-hold amplifier 100 and the analog-to-digital converter 102. However, such a system for monitoring and recording cell cultures would merely employ a different, well know technique for determining the delay period for its alternating current voltage that i is equal to an interval of time between the alternating current voltage having an instantaneous potential of zero volts and having an instantaneous potential equal to the maximum voltage of the alternating current voltage.

Although the invention has been described with respect to particular embodiments and features, it will be appreciated that various changes and modifications can be made without departing from the invention. As an example, and in another preferred embodiment, the probes are inserted into the well from the bottom of the well to allow for easy serialization of the unit and minimal media volume.

What is claimed:

1. A high throughput screening method comprising placing cells on a substrate defining a plurality of discrete microwells on a substrate surface, at a well density of greater than about 100/cm$^2$, with the number of cells in each well being less than about 10$^3$, where the cells in each well have been exposed to a selected agent, and determining the conductance in each well, by applying a low-voltage, AC signal across a pair of electrodes placed in that well, and synchronously measuring the conductance across the electrodes, to monitor the level of growth or metabolic activity of cells contained in each well.

2. The method of claim 1, wherein the signal applied across the electrodes is between 5 and 10 mV.

3. The method of claim 1, wherein said measuring includes measuring the conductance in the medium at a selected phase angle of the signal.

4. The method of claim 1, wherein said measuring is designed to measure the conductance of the medium at a measuring frequency which is at least an order of magnitude greater than that of said signal.

5. The method of claim 1, wherein the wells contain at most 10–100 cells.

* * * * *